(12) United States Patent
Kamei

(10) Patent No.: US 10,422,893 B2
(45) Date of Patent: Sep. 24, 2019

(54) RADIATION IMAGING APPARATUS

(71) Applicant: CANON KABUSHIKI KAISHA, Tokyo (JP)

(72) Inventor: Satoshi Kamei, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 267 days.

(21) Appl. No.: 15/598,424

(22) Filed: May 18, 2017

(65) Prior Publication Data

US 2017/0343683 A1 Nov. 30, 2017

(30) Foreign Application Priority Data

May 26, 2016 (JP) .................................. 2016-105444

(51) Int. Cl.
*H05G 1/54* (2006.01)
*G01T 1/24* (2006.01)
(Continued)

(52) U.S. Cl.
CPC .............. *G01T 1/244* (2013.01); *G01T 1/243* (2013.01); *G01T 1/247* (2013.01);
(Continued)

(58) Field of Classification Search
CPC ...... G01N 23/223; G01N 21/67; G01N 23/04; G01T 1/243; G01T 1/244; G01T 1/247;
(Continued)

(56) References Cited

U.S. PATENT DOCUMENTS 7,421,063 B2 *  9/2008  Takenaka ................ G01T 1/244
                                                  378/116
8,754,380 B2 *  6/2014  Omura ................. A61B 6/5205
                                                  250/336.1

(Continued)

FOREIGN PATENT DOCUMENTS

CN      103575406       2/2014
JP      2002-344809     11/2002
(Continued)

OTHER PUBLICATIONS

European Extended Search Report dated Oct. 20, 2017 in counterpart application No. 17168640.5.

*Primary Examiner* — Irakli Kiknadze
(74) *Attorney, Agent, or Firm* — Venable LLP

(57) ABSTRACT

A radiation imaging apparatus, comprising a sensor array and a controller, wherein the controller shifts to a non-capturing mode upon receiving an instruction representing a suspension of radiographic imaging, and shifts to a capturing mode upon receiving an instruction representing a start of radiographic imaging, and the controller performs, in the capturing mode, one of movie capturing and continuous capturing in which an operation of driving the sensor array in response to one radiation irradiation for the sensor array and acquiring image data of one frame from the sensor array is repetitively executed, and, in the non-capturing mode, drives the sensor array to suppress lowering of a temperature of the sensor array in the non-capturing mode from the temperature of the sensor array in the capturing mode.

10 Claims, 9 Drawing Sheets

(51) Int. Cl.
| | |
|---|---|
| *H01L 27/146* | (2006.01) |
| *H04N 5/32* | (2006.01) |
| *H04N 5/357* | (2011.01) |
| *G01N 23/223* | (2006.01) |

(52) U.S. Cl.
CPC ......... *H01L 27/14658* (2013.01); *H04N 5/32* (2013.01); *H04N 5/357* (2013.01); *G01N 23/223* (2013.01)

(58) Field of Classification Search
CPC ............. G01T 1/2018; H01L 27/14658; H01L 2924/0002; H01L 2924/00; H01L 23/34; H01L 27/14659; H01L 27/14663; H04N 5/32; H04N 5/357; H04N 5/361; H04N 5/378; H04N 5/3205; H04N 5/3698; H04N 5/374; H04N 5/347; H04N 5/367; H04N 5/16; H04N 5/21; H04N 5/325; G01K 7/01; A61B 6/04; A61B 6/06; A61B 6/4283; A61B 6/4291; A61B 6/4476; A61B 6/5241; A61B 6/542; G01D 18/002; G01D 18/004; G01D 18/006; G01D 18/008; H05G 1/64
USPC .................. 378/114–116, 19, 98.9, 145, 209
See application file for complete search history.

(56) References Cited

U.S. PATENT DOCUMENTS

| | | | |
|---|---|---|---|
| 9,082,168 B2 * | 7/2015 | Hiroike | ................. G06T 7/0012 |
| 9,369,639 B2 * | 6/2016 | Kobayashi | ........... H04N 5/2178 |
| 2002/0190215 A1 | 12/2002 | Tashiro et al. | ........... 250/370.11 |
| 2007/0158575 A1 | 7/2007 | Heismann et al. | ...... 250/370.15 |
| 2011/0110497 A1 * | 5/2011 | Nishino | ................... A61B 6/04 |
| | | | 378/98.8 |
| 2014/0042319 A1 | 2/2014 | Pickett et al. | |
| 2016/0134818 A1 | 5/2016 | Iwashita et al. | ............... 348/162 |
| 2016/0139276 A1 | 5/2016 | Naito | ............................ 250/393 |

FOREIGN PATENT DOCUMENTS

| | | |
|---|---|---|
| JP | 2007220087 A | 8/2007 |
| JP | 2009-293974 | 12/2009 |
| JP | 2010-112866 A | 5/2010 |
| JP | 2011-101693 A | 5/2011 |
| JP | 2015019157 A | 1/2015 |
| WO | 2010/004776 A1 | 1/2010 |

* cited by examiner

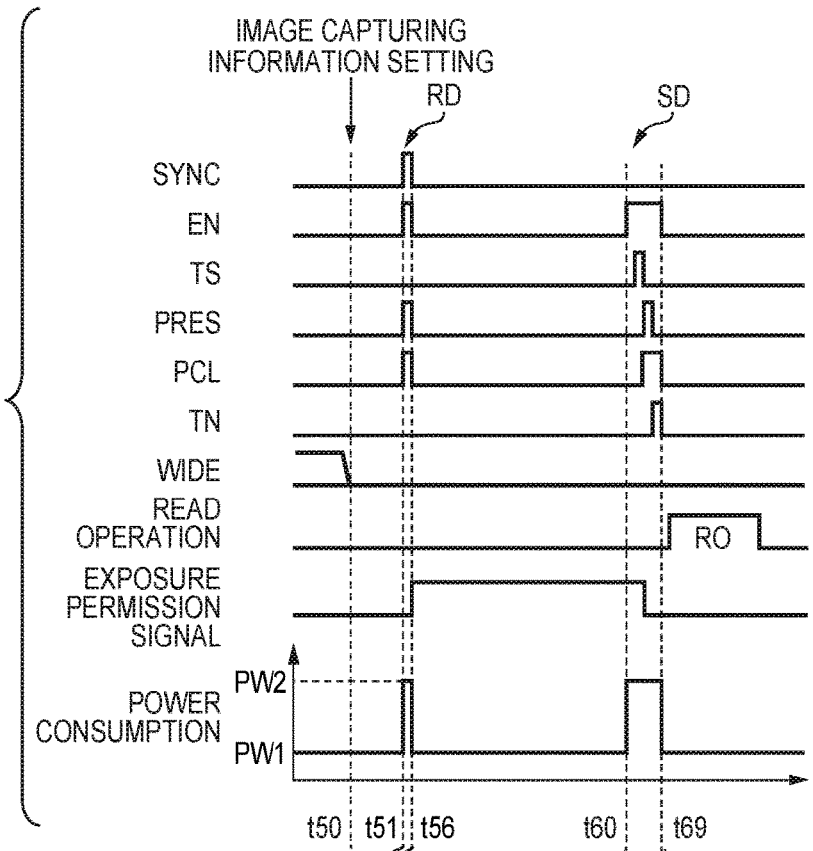
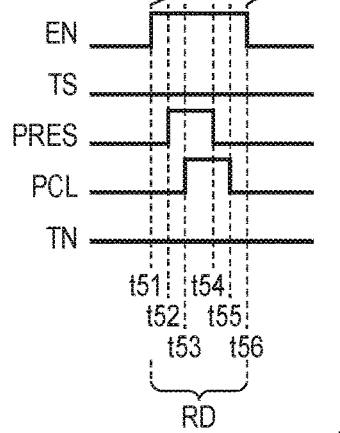
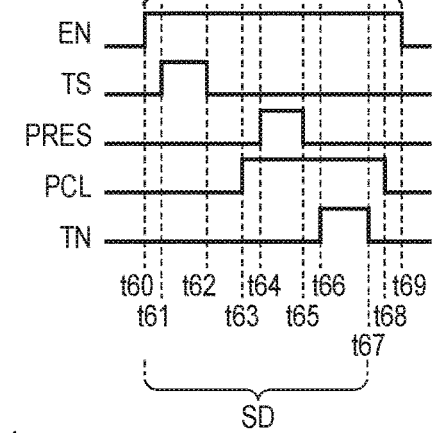
FIG. 6A
FIG. 6B
FIG. 6C

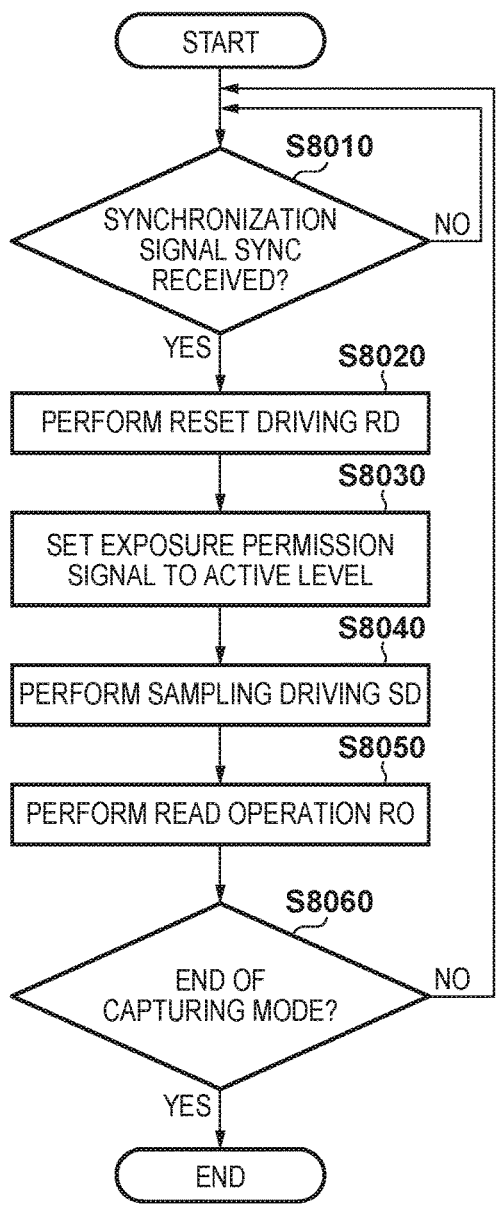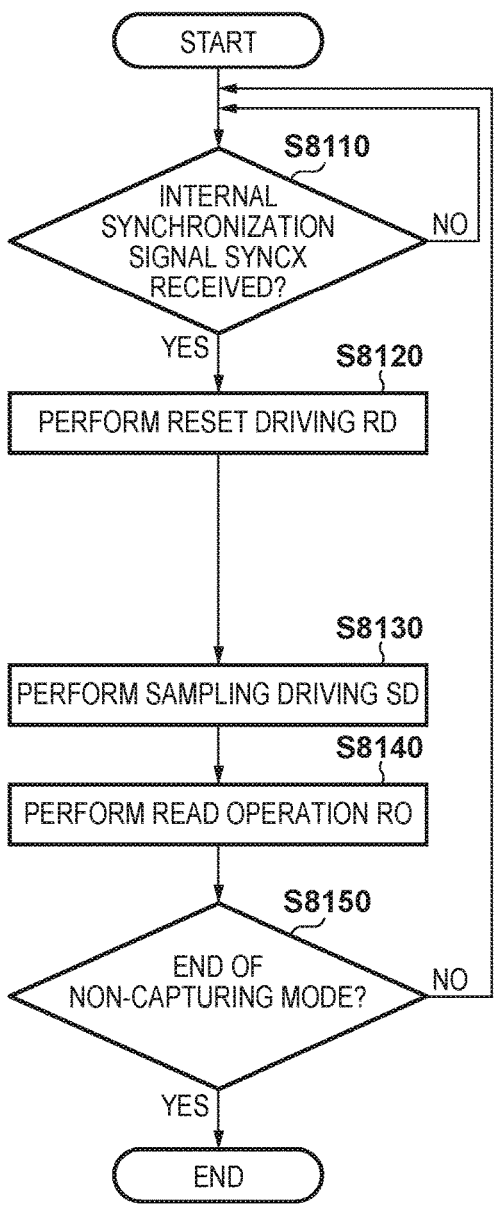

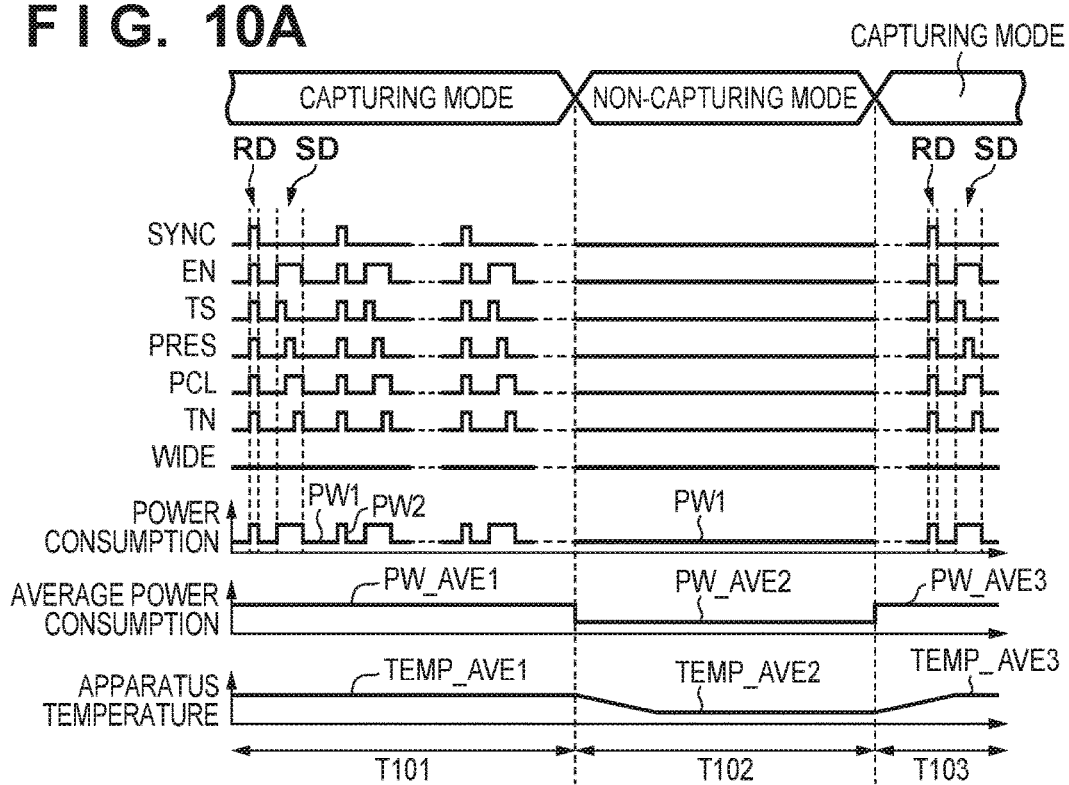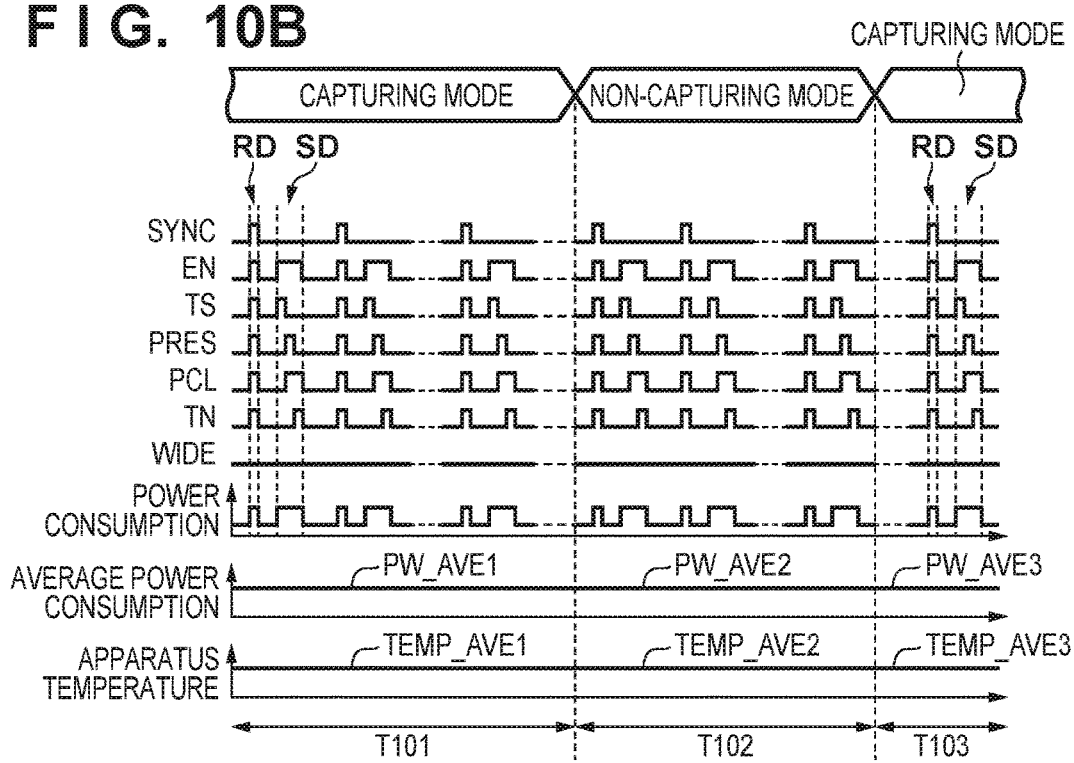

RADIATION IMAGING APPARATUS

BACKGROUND OF THE INVENTION

Field of the Invention

The present invention relates to a radiation imaging apparatus.

Description of the Related Art

A radiation imaging apparatus includes, for example, a plurality of sensors that generate signals corresponding to the amount of a radiation, and a driver that drives the plurality of sensors (see Japanese Patent Laid-Open No. 2002-344809). In radiographic imaging, the plurality of sensors are irradiated with a radiation for a predetermined period. After that, the driver drives the plurality of sensors to read signals corresponding to the amount of radiation irradiation from the plurality of sensors. The group of the read signals is used to form the image data (frame data) of one frame. In movie capturing or continuous capturing, the series of operations including radiation irradiation, signal read from the plurality of sensors, and formation of frame data described above is executed a plurality of times (repetitively).

It can be considered that the series of operations repetitively executed is temporarily suspended when, for example, image capturing is paused to observe details of a morbid portion in movie capturing, or image capturing is suspended to change the angle of observation of a morbid portion in continuous capturing. Since the plurality of sensors and the driver are at rest (more specifically, a state in which the levels of signals in the plurality of sensors and the driver do not change) during this time, it can be considered that the apparatus temperature lowers because of a temporary decrease in power consumption. If the apparatus temperature lowers, noise components in the plurality of sensors change. Hence, when the image capturing is resumed, image quality may change.

SUMMARY OF THE INVENTION

The present invention provides a technique advantageous in reducing a variation in image quality when resuming radiographic imaging.

One of the aspects of the present invention provides a radiation imaging apparatus, comprising a sensor array and a controller, wherein the controller shifts to a non-capturing mode upon receiving an instruction representing a suspension of radiographic imaging, and shifts to a capturing mode upon receiving an instruction representing a start of radiographic imaging, and the controller performs, in the capturing mode, one of movie capturing and continuous capturing in which an operation of driving the sensor array in response to one radiation irradiation for the sensor array and acquiring image data of one frame from the sensor array is repetitively executed, and in the non-capturing mode, drives the sensor array to suppress lowering of a temperature of the sensor array in the non-capturing mode from the temperature of the sensor array in the capturing mode.

Further features of the present invention will become apparent from the following description of exemplary embodiments with reference to the attached drawings.

BRIEF DESCRIPTION OF THE DRAWINGS

FIGS. 6A to 6C are views for explaining an example of a sensor chip driving method;

FIGS. 8A and 8B are flowcharts for explaining examples of operation modes of an image capturing controller;

FIGS. 10A and 10B are timing charts for explaining an example of a single sensor driving method and a comparative example.

DESCRIPTION OF THE EMBODIMENTS

Figure 1:
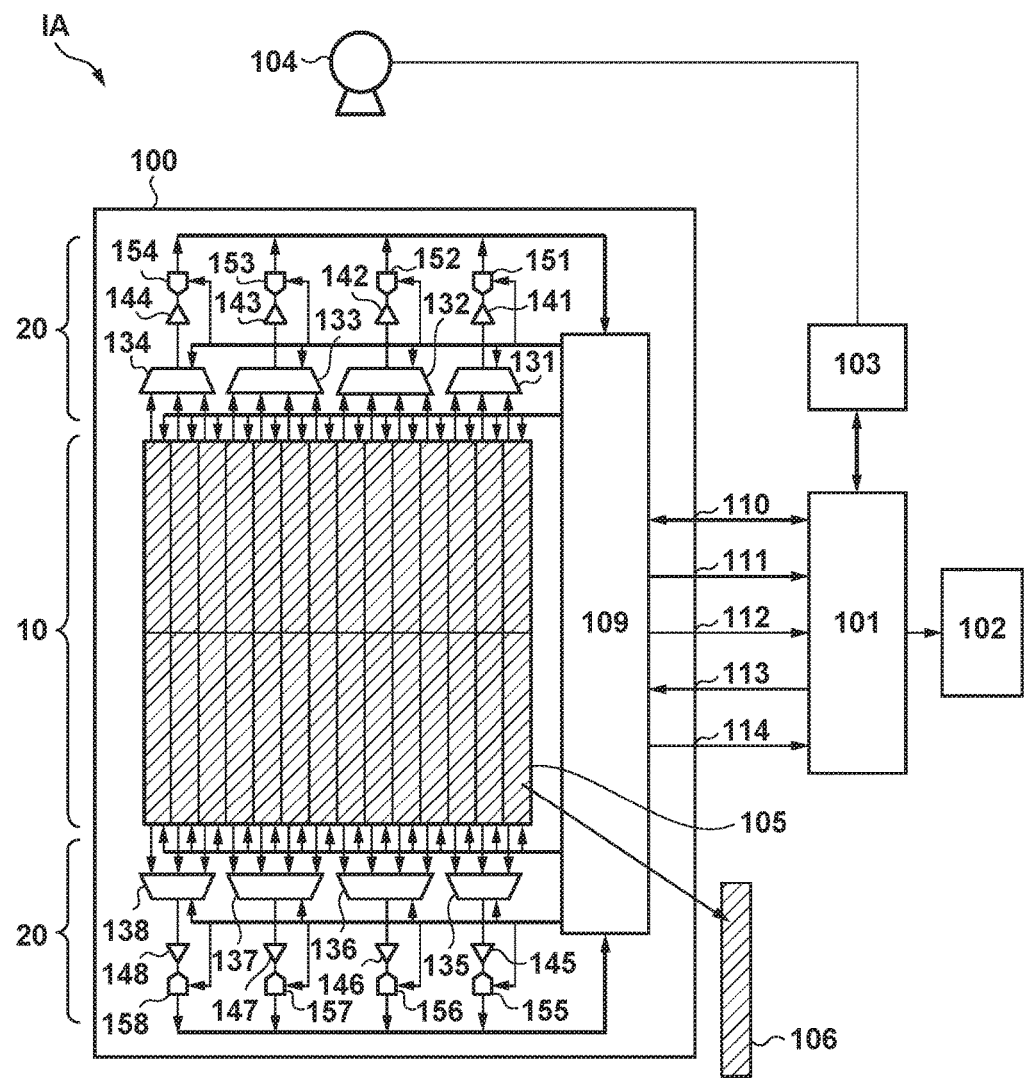
FIG. 1 is a view for explaining an example of the system arrangement of a radiation imaging apparatus.

A preferred embodiment of the present invention will now be described with reference to the accompanying drawings. The same reference numerals denote the same elements throughout the drawings, and a description of repetitive contents will be omitted hereinafter. Note that the drawings are illustrated for the purpose of only explaining a structure or an arrangement, and the sizes of illustrated elements do not always reflect actual sizes.

FIG. 1 is a system block diagram showing an example of the overall arrangement of a radiation imaging apparatus IA (to be referred to as an "apparatus IA" hereinafter). The apparatus IA is a fluoroscopic examination apparatus, for example, a C-arm type fluoroscopic apparatus configured to observe the inside of the body of a subject (object) such as a patient from various angles by movie capturing or continuous capturing. The apparatus IA includes an image capturing device 100, a controller 101, a display 102, a radiation source controller 103, and a radiation source 104. The image capturing device 100 acquires image data representing an image of the inside of the body of a subject by radiographic imaging (or image capturing), and outputs the image data to the controller 101, as will be described later in detail.

The controller 101 functions as a system controller that performs synchronous control of the entire apparatus IA by transmitting/receiving an instruction by a control signal or control command to/from the units (the units can include not only those illustrated but also units that are not illustrated). The controller 101 also functions as a processor that receives image data from the image capturing device 100 and performs image processing or data processing. An input terminal (not shown) can be connected to the controller 101. A user can input image capturing information (for example, setting information necessary for image capturing such as an operation mode, a frame rate, and other parameters, which may be expressed as image capturing conditions) to the controller 101 using the input terminal. The controller 101 synchronously controls the units based on the input image capturing information.

The controller 101 is a computer including a CPU and memories but may be a computer storing a program or software to implement each operation to be described in this specification, or an arithmetic unit including an integrated circuit (for example, an ASIC or FPGA). In other words, the functions of the controller 101 to be described in this specification are implemented by hardware and/or software.

The display 102 is, for example, a liquid crystal display, and displays a radiographic image based on image data from the controller 101. A user such as a doctor can make a diagnosis for a subject while referring to the radiographic image displayed on the display 102.

The radiation source controller 103 can be controlled by the controller 101 so as to synchronize with the image capturing device 100. The radiation source controller 103 outputs a signal to do radiation irradiation to the radiation source 104 in response to a control signal from the controller 101. In response to the signal from the radiation source controller 103, the radiation source 104 generates a radiation (typically, x-rays are used, but α-rays or β-rays may be used) to do radiographic imaging. The generated radiation passes through the subject (not shown) and enters the image capturing device 100.

The start of radiographic imaging may be executed by the user via the input terminal but may be executed using an exposure switch that can be provided on the radiation source controller 103. For example, if an instruction (command) to start radiographic imaging is input, the controller 101 synchronously controls the units to cause the radiation source 104 to generate a radiation and cause the image capturing device 100 to detect the generated radiation and output image data.

The image capturing device 100 includes a sensor unit 10 that detects a radiation, a reader 20 that reads a signal from the sensor unit 10, and an image capturing controller 109 that controls the units in the image capturing device 100 while transmitting/receiving a control signal or control command to/from the controller 101.

In this example, the sensor unit 10 includes a sensor array 105 formed by arranging a plurality of sensor chips 106, and forms an imaging plane configured to acquire a radiographic image. As each sensor chip 106, for example, a CMOS image sensor chip formed by a known semiconductor manufacturing process using a semiconductor wafer such as a silicon wafer can be used. In each sensor chip 106, a plurality of sensors (to be referred to as "sensor s") are arranged in an array (to form a plurality of rows and a plurality of columns). According to this arrangement, upsizing of the sensor array 105 can be implemented. Note that an arrangement in which the sensor chips 106 are arranged to form 2 rows×14 columns will be exemplified here for a descriptive convenience. However, the number of rows and the number of columns are not limited these values.

The sensor chips 106 adjacent to each other may be separated physically by dicing or not. For example, the sensor chips 106 formed on a semiconductor wafer are inspected before dicing, and the sensor chips 106 whose inspection results satisfy a predetermined condition are arrayed to form the sensor array 105. Note that the sensor array 105 can be formed by arranging the plurality of sensor chips 106 on a plate-shaped member such as a base or a support plate. From this viewpoint, the sensor array 105 may be expressed as a sensor panel, a sensor substrate, or the like.

The sensor unit 10 can also include a scintillator (not shown) that converts a radiation into light. Light from the scintillator is detected, and an electrical signal corresponding to the light is obtained by photoelectric conversion. A so-called indirect conversion type structure that converts a radiation into light by a scintillator will be considered here. However, the present invention is also applicable to a so-called direct conversion type structure that (directly) converts a radiation into an electrical signal.

A plurality of electrodes (not shown) used for signal transmission/reception or power supply can be arranged on the sensor unit 10. The sensor unit 10 can be connected to external circuits via the plurality of electrodes by a flying lead type printed board. With this arrangement, for example, signals from the sensor unit 10 are read by the reader 20 via the electrodes. In addition, a control signal from the image capturing controller 109 is supplied to the sensor unit 10 via the electrodes.

The reader 20 includes, for example, multiplexers 131 to 138, signal amplifiers 141 to 148, and A/D converters 151 to 158. Each of the multiplexer 131 and the like functions as a selector configured to select a sensor as a signal read target based on a predetermined unit. For example, each of the multiplexer 131 and the like selects a sensor as a signal read target for each sensor chip 106 or for each column. Each of the signal amplifier 141 and the like and the A/D converter 151 and the like functions as an output unit configured to output the signal of each sensor (sensor signal) as the selection target. For example, each of the signal amplifier 141 and the like amplifies a signal by a differential amplifier or the like, and each of the A/D converter 151 and the like analog-to-digital converts (A/D-converts) the amplified signal.

The image capturing controller 109 transmits/receives an instruction by a control signal or control command to/from the controller 101 via various kinds of interfaces. When performing radiographic imaging, the image capturing controller 109 performs image capturing using the sensor unit 10 and the reader 20. As the various kinds of interfaces, known communication means are used. A wired communication means such as a LAN may be used, or a wireless communication means such as a Wi-Fi may be used. After that, the image capturing controller 109 reads sensor signals from the sensor unit 10, forms image data based on the read sensor signals, and outputs the image data to the controller 101.

A control interface 110 is an interface configured to implement control of the image capturing device 100 by the controller 101 by transmitting/receiving image capturing information input by the user and apparatus information such as the operation state of the image capturing device 100. An image data interface 111 is an interface configured to output image data from the image capturing device 100 to the controller 101. The image capturing controller 109 notifies the controller 101 that the image capturing device 100 is set in a state to start radiographic imaging by supplying a READY signal via an interface 112. During the time in which the READY signal from the image capturing controller 109 is active, the controller 101 notifies the image capturing controller 109 of the timing to start one radiographic imaging by supplying a synchronization signal (synchronization signal SYNC) via an interface 113. The image capturing controller 109 requests the controller 101 to start radiation irradiation by supplying an exposure permission signal via an interface 114. During the time in which the exposure permission signal is active, the controller 101 causes the radiation source 104 to generate a radiation via the radiation source controller 103.

In this example, the controller 101 generally controls the entire system of the apparatus IA. On the other hand, the image capturing controller 109 controls the operation of the image capturing device 100 based on an instruction by a control signal or control command from the controller 101. An arrangement in which the controller 101 and the image capturing controller 109 are separated has been described here. However, these functions may be formed by a single unit. For example, the controller 101 or part of the controller 101 can be incorporated in the image capturing device 100, and the image capturing controller 109 and the controller 101 may simply be referred to as a controller as a whole.

Radiographic imaging can be implemented by the above-described arrangement. In the image capturing device 100, sensor signals read from the sensor unit 10 are composited into frame data (image data of one frame) by the image capturing controller 109, and the frame data is output to the controller 101. In another example, the sensor signals read from the sensor unit 10 may be output to the controller 101 and composited into frame data by the controller 101. The controller 101 performs predetermined image processing or data processing for the image data, and causes the display 102 to display a radiographic image based on the image data, as described above.

Each unit in the apparatus IA is not limited to the above-described arrangement. The arrangement of each unit may appropriately be changed in accordance with the purpose or the like. For example, the controller 101 and the image capturing controller 109 can be formed by a single unit, as described above. This also applies to the remaining units. That is, the functions of two or more units may be implemented by one unit, or some functions of a given unit may be implemented by another unit.

Figure 2:
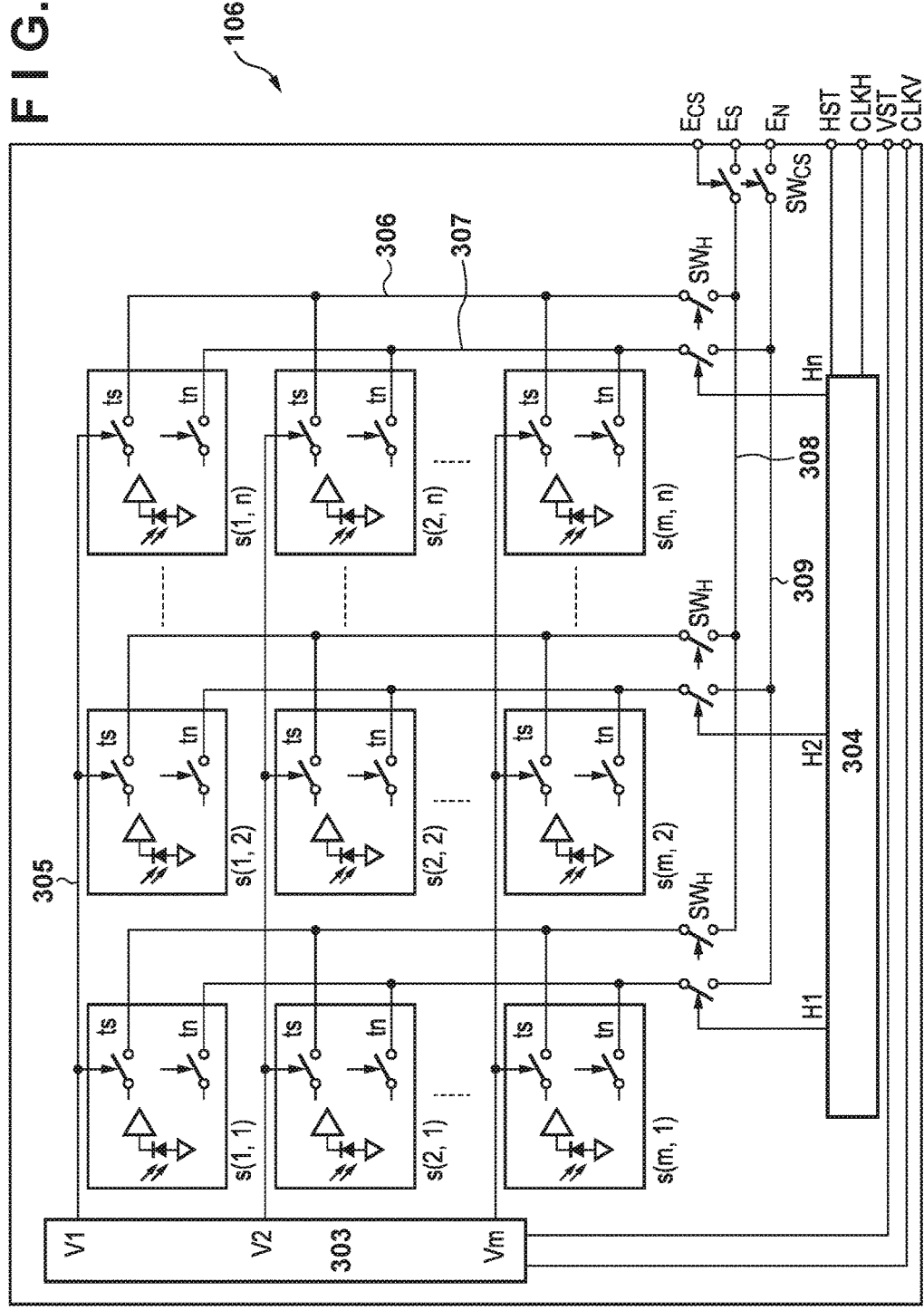
FIG. 2 is a view for explaining an example of the arrangement of a sensor array.

FIG. 2 shows an example of the arrangement of the single sensor chip 106. Each sensor chip 106 includes a plurality of sensors s, a vertical scanning circuit 303 configured to drive the plurality of sensors s, and a horizontal scanning circuit 304 configured to read signals from the plurality of sensors s.

In each sensor chip 106, the plurality of sensors s are arranged to form, for example, m rows×n columns. In FIG. 2, for example, a sensor on the first row and the second column is represented by "s(1, 2)". Each sensor s holds an S signal corresponding to a signal component and an N signal corresponding to a noise component, and the S signal and the N signal are individually output from each sensor s, as will be described later in detail.

Each of the vertical scanning circuit 303 and the horizontal scanning circuit 304 is formed by, for example, a shift register, and operates based on a control signal from the image capturing controller 109. The vertical scanning circuit 303 functions as a driver that drives the sensors s of the signal read target on a row basis based on a control signal from the image capturing controller 109. More specifically, the vertical scanning circuit 303 supplies a drive signal to the plurality of sensors s via control lines 305, and drives the plurality of sensors s on a row basis based on the drive signal. The horizontal scanning circuit 304 causes the sensors s of each column to sequentially output signals based on a control signal from the image capturing controller 109 (also called "horizontal transfer"). More specifically, the horizontal scanning circuit 304 causes the sensors s driven by the vertical scanning circuit 303 to sequentially output signals (the S signals and the N signals) to the outside via column signal lines 306 and 307 and analog output lines 308 and 309.

The sensor chip 106 includes a terminal $E_S$ configured to read the S signal held by each sensor s, and a terminal $E_N$ configured to read the N signal held by each sensor s. The sensor chip 106 also includes a select terminal $E_{CS}$. If the signal received by the terminal $E_{CS}$ changes to active level, the signals of each sensor s of the sensor chip 106 are read via the terminals $E_S$ and $E_N$.

More specifically, each sensor s includes a terminal ts configured to output an S signal and a terminal tn configured to output an N signal. The terminal ts is connected to the column signal line 306, and the terminal tn is connected to the column signal line 307. The column signal lines 306 and 307 are connected to the analog output lines 308 and 309, respectively, via switches $SW_H$ to be turned on in response to a control signal from the horizontal scanning circuit 304. The signals of the analog output lines 308 and 309 are output from the terminals $E_S$ and $E_N$, respectively, via switches $SW_{CS}$ to be turned on in response to a signal received by the terminal $E_{CS}$.

The sensor chip 106 also includes a terminal VST and the like which receive control signals to control the vertical scanning circuit 303 and the horizontal scanning circuit 304. The terminal VST receives a start pulse to be input to the vertical scanning circuit 303. A terminal CLKV receives a clock signal to be input to the vertical scanning circuit 303. A terminal HST receives a start pulse to be input to the horizontal scanning circuit 304. A terminal CLKH receives a clock signal to be input to the horizontal scanning circuit 304. These control signals are supplied from the image capturing controller 109.

With the above-described arrangement, in the sensor chip 106, the sensors s are controlled on a row basis, and the signals (the S signals and the N signals) of the sensors s on each column are sequentially outputs, thereby performing signal read.

Figure 3:
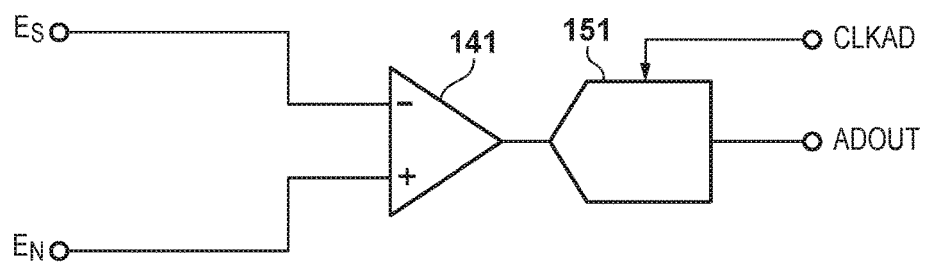
FIG. 3 is a view for explaining an example of the arrangement of a reader.

FIG. 3 shows part of the circuit arrangement of the reader 20. A signal from the terminal $E_S$ is input to the inverting input terminal (indicated by "−" in FIG. 3) of the signal amplifier 141, and a signal from the terminal $E_N$ is input to the noninverting input terminal (indicated by "+" in FIG. 3) of the signal amplifier 141. The signal amplifier 141 amplifies the difference (signal value difference) between the signal from the terminal $E_S$ and the signal from the terminal $E_N$, and outputs a signal corresponding to the difference to the A/D converter 151. The A/D converter 151 receives a clock signal by a terminal CLKAD, and A/D-converts (analog-to-digital converts) the signal from the signal amplifier 141 based on the clock signal. The A/D-converted signal is output as a sensor signal to the image capturing controller 109 via a terminal ADOUT.

Note that the description has been made here by referring to only the signal amplifier 141 and the A/D converter 151 for the descriptive convenience (the multiplexer 131 is not illustrated). However, this description also applies to a case in which the multiplexer 131 is further included.

Figure 4:
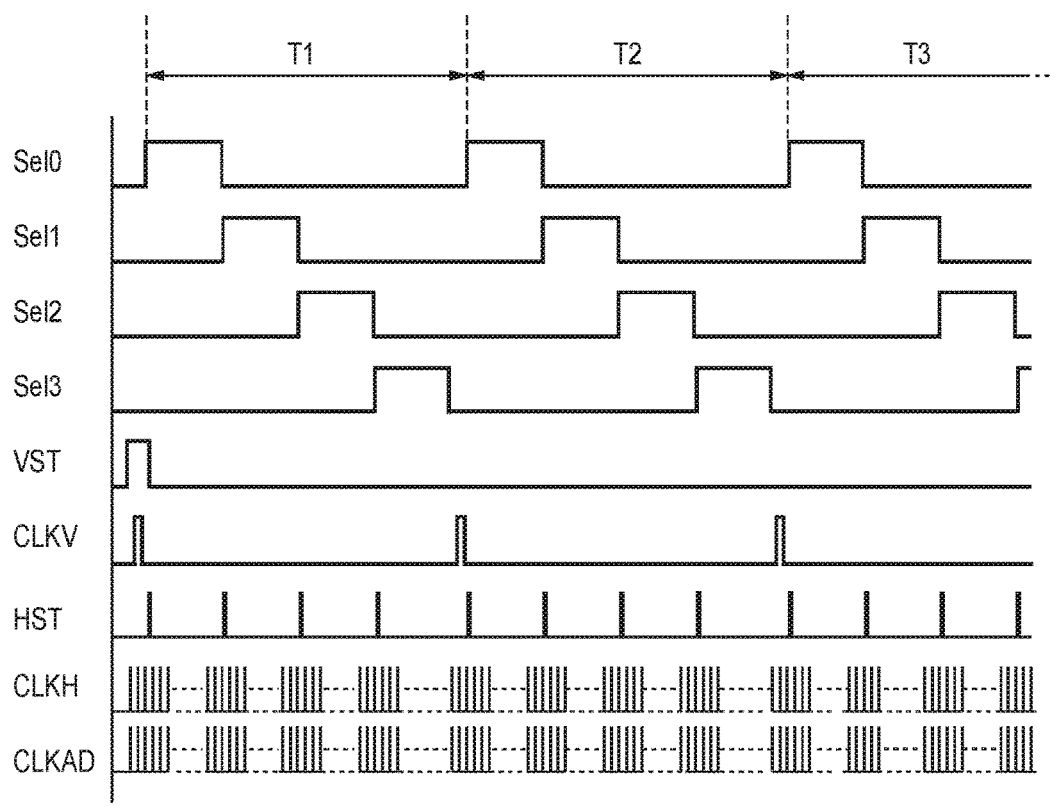
FIG. 4 is a timing chart for explaining an example of an image data read method.

FIG. 4 shows an example of a timing chart for explaining a read operation (to be referred to as a read operation RO hereinafter) of reading a signal from the image capturing device 100. The abscissa represents the time axis, and control signals are plotted along the ordinate. For the descriptive convenience, a case in which signals are read from four sensor chips 106 (sensor chips $106_0$ to $106_3$) will be explained.

A selection signal Sel (Sel0 to Sel3) is a control signal to select the sensor chip 106 as a signal read target. The selection signals Sel0 to Sel3 correspond to the sensor chips $106_0$ to $106_3$ and are input to the terminals $E_{CS}$ of the corresponding sensor chips 106, respectively. For example, if the sensor chip $106_1$ is the signal read target, the selection signal Sel1 is set to high level (H level), and the remaining selection signals Sel0, Sel2, and Sel3 are set to low level (L level).

Remaining control signals VST and the like are control signals input to the terminals. For example, a control signal input to the terminal VST will be referred to as the signal VST. This also applies to the remaining control signals.

The signal VST is a start pulse signal for row selection. Based on this signal, the sensors s of the first row in the sensor chip 106 selected by the selection signal Sel are selected by the vertical scanning circuit 303. The signal CLKV is a clock signal. Every time the clock signal is received by the terminal CLKV, the selected row is sequentially shifted from the first row to the mth row (that is, the sensors s are selected on a row basis sequentially from the first row to the mth row).

The signal HST is a start pulse signal for column selection. Based on this signal, the sensors s of the first column in the sensor chip 106 selected by the selection signal Sel are selected by the horizontal scanning circuit 304. The signal CLKH is a clock signal. Every time the clock signal is received by the terminal CLKH, the selected column is sequentially shifted from the first column to the nth column (that is, the sensors s are selected on a column basis sequentially from the first column to the nth column).

The signal CLKAD is a clock signal. As described above, based on this signal, a signal corresponding to the difference between the S signal and the N signal in each sensor s is A/D-converted by an A/D converter 108.

First, the signals VST and CLKV change to H level. After that, the selection signals Sel0 to Sel3 sequentially change to H level, and the sensor chips $106_0$ to $106_3$ are sequentially selected. The signal HST changes to H level at a timing when a certain selection signal Sel changes to H level (or after the change to H level), the signal HST changes to H level. After that, the clock signals CLKH and CLKAD are input until the next selection signal Sel changes to H level.

By this driving method, for example, in a first period T1 shown in FIG. 4, signal read from the sensors s of the first row is performed in each of the sensor chips $106_0$ to $106_3$. More specifically, first, for the sensors s of the first row in the sensor chip $106_0$, the signals of the sensors s are sequentially A/D-converted from the first column to the nth column. Next, the signals of the sensors s of the first row in the sensor chip $106_1$ are similarly A/D-converted. After that, the signals of the sensors s of the first row in the sensor chip $106_2$ are similarly A/D-converted, and then, the signals of the sensors s of the first row in the sensor chip $106_3$ are similarly A/D-converted. The same operation as in the first period T1 is performed in a second period T2 (signal read from the sensors s of the second row in each sensor chip 106), a third period T3 (signal read from the sensors s of the third row in each sensor chip 106), and subsequent periods (from T4 (not shown)).

The read operation RO is performed in this way. Note that the read operation RO may be called output driving of outputting the signals of the sensors s from the viewpoint of the vertical scanning circuit 303 functioning as a driver, the image capturing controller 109 that controls the operation of the vertical scanning circuit 303, or the controller 101 that performs general control.

Figure 5:
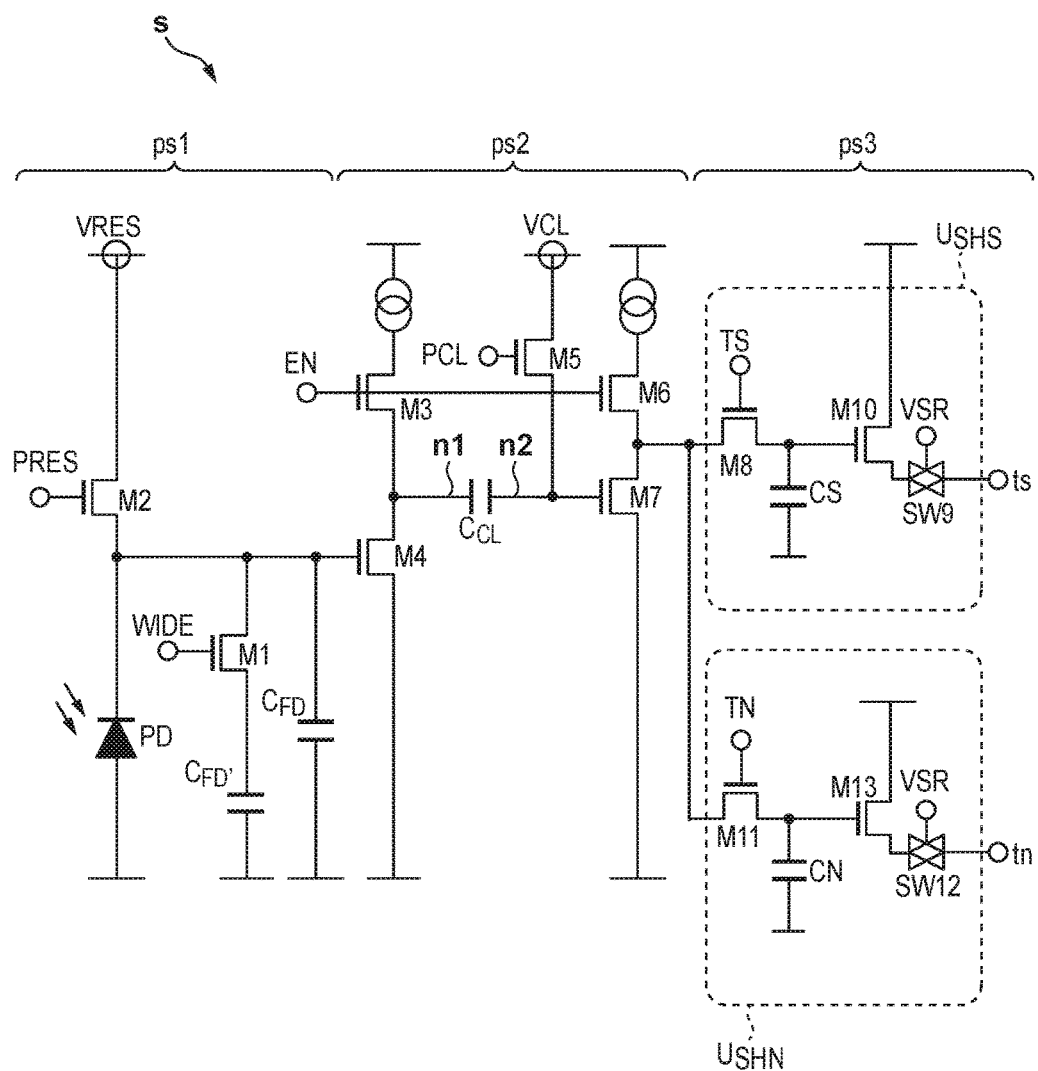
FIG. 5 is a view for explaining an example of the arrangement of a single sensor (pixel)

FIG. 5 shows the circuit arrangement of single sensor s. The sensor s includes a first portion ps1, a second portion ps2, and a third portion ps3.

The first portion psi includes a photodiode PD, transistors M1 and M2, a floating diffusion capacitor $C_{FD}$ (to be referred to as an FD capacitor $C_{FD}$ hereinafter), and a capacitor $C_{FD}'$ for sensitivity switching.

The photodiode PD is a photoelectric conversion element, and converts light (scintillator light) generated by the above-described scintillator into an electrical signal in accordance with radiation irradiation. More specifically, the photodiode PD generates charges in an amount corresponding to the amount of scintillator light, and a voltage of the FD capacitor $C_{FD}$ corresponding to the generated charge amount is output to the second portion ps2.

As described above, assuming the indirect conversion type sensor unit 10, an arrangement that uses the photodiode PD as a detection element configured to detect a radiation has been exemplified here. However, another photoelectric conversion element may be used.

The capacitor $C_{FD}'$ for sensitivity switching is used to switch the sensitivity of the sensor s to a radiation, and is connected to the photodiode PD via the transistor (switch element) M1. If a signal WIDE changes to active level, the transistor M1 is turned on, and the voltage of the combined capacitance of the FD capacitor $C_{FD}$ and the capacitor $C_{FD}'$ is output to the second portion ps2. That is, if the signal WIDE is at H level, the sensor s is in a low sensitivity mode. If the signal WIDE is at L level, the sensor s is in a high sensitivity mode. With this arrangement, the sensitivity to a radiation can be changed.

If a signal PRES changes to active level, the transistor M2 resets (initializes) the charges in the photodiode PD to reset the voltage output to the second portion ps2.

The second portion ps2 includes transistors M3 to M7, a clamp capacitor $C_{CL}$, and a constant current source (for example, a transistor of a current mirror structure). The transistors M3 and M4 and the constant current source are connected in series to form a current path. If an enable signal EN input to the gate of the transistor M3 changes to active level, the transistor M4 that receives the voltage from the first portion ps1 performs a source follower operation, and outputs a voltage corresponding to the voltage from the first portion ps1.

A clamp circuit formed from the transistors M5 to M7 and the clamp capacitor $C_{CL}$ is arranged at the subsequent stage. More specifically, one terminal n1 of the clamp capacitor $C_{CL}$ is connected to the node between the transistor M3 and the transistor M4 of the first portion ps1, and the other terminal n2 is connected to a clamp voltage VCL via the transistor M5. The transistors M6 and M7 and the constant current source are connected in series to form a current path. The terminal n2 is connected to the gate of the transistor M7.

With this arrangement, kTC noise (so-called reset noise) generated in the photodiode PD of the first portion ps1 is removed. More specifically, the voltage corresponding to the voltage from the first portion ps1 at the time of reset described above is input to the terminal n1 of the clamp capacitor $C_{CL}$. If a clamp signal PCL changes to active level, the transistor M5 is turned on, and the clamp voltage VCL is input to the terminal n2 of the clamp capacitor $C_{CL}$. The potential difference across the terminals n1 and n2 of the clamp capacitor $C_{CL}$ is thus clamped as a noise component. In other words, the second portion ps2 functions as a holding portion that holds, by the clamp capacitor $C_{CL}$, the voltage corresponding to the charges generated in the photodiode PD, which is a voltage corresponding to kTC noise. In this arrangement, the second portion ps2 holds a voltage obtained by removing the clamped noise component from the voltage output, according to the charges generated in the photodiode PD, from the transistor M4 for performing the source follower operation.

The enable signal EN is supplied to the gate of the transistor M6. If the enable signal EN changes to active level, the transistor M7 performs a source follower operation, and outputs a voltage corresponding to the gate voltage of the transistor M7 to the third portion ps3. For example, if charges are generated in the photodiode PD, the gate voltage of the transistor M7 changes, and a voltage corresponding to the changed voltage is output to the third portion ps3.

The third portion ps3 includes transistors M8, M10, M11, and M13, analog switches SW9 and SW12, and capacitors CS and CN. A unit formed by the transistors M8 and M10, the analog switch SW9, and the capacitor CS is called a "first unit $U_{SHS}$".

In the first unit $U_{SHS}$, the transistor M8 and the capacitor CS form a sample hold circuit. More specifically, the state (the ON state or OFF state) of the transistor M8 is switched using a control signal TS, thereby holding the signal from the second portion ps2 as the S signal. In other words, the first unit $U_{SHS}$ functions as a first sampling unit that samples the S signal. The transistor M10 performs a source follower operation, and the S signal is thus amplified. The amplified S signal is output from the terminal ts by turning on the analog switch SW9 using a control signal VSR.

Like the first unit $U_{SHS}$, the transistors M11 and M13, the analog switch SW12, and the capacitor CN form a "second unit $U_{SHN}$" that outputs a signal from the terminal tn. In the second unit $U_{SHN}$, the N signal is held by the capacitor CN. In other words, the second unit $U_{SHN}$ functions as a second sampling unit that samples the N signal. As described above, the reader 20 reads the difference between the S signal and the N signal via the terminals ts and tn. Fitted pattern noise (FPN) derived from the second portion ps2 is thus removed.

With the above-described arrangement, the S signal and the N signal are held by the capacitors CS and CN, respectively. The held S signal and the N signal are read by so-called nondestructive read by turning on the analog switches SW9 and SW12, respectively. That is, during the OFF state of the transistors M8 and M11, the held S signal and the N signal can be read at an arbitrary timing.

FIGS. 6A to 6C show the driving method (timing charts) of the sensor chip 106 in a case in which radiographic imaging is performed once (in a case in which image data of one frame is acquired). That is, a series of operations to be described below is an example of the driving method in a still image capturing. Movie capturing or continuous capturing is implemented by repetitively executing the series of operations. Note that for the descriptive convenience, a case in which the high sensitivity mode is set (that is, the signal WIDE is at L level) will be described below.

As shown in FIG. 6A, at time t50, image capturing information (setting information necessary for image capturing such as an operation mode, a frame rate, and other parameters) is set. Next, at times t51 to t56, reset driving RD to reset the sensors s and the clamp capacitor $C_{CL}$ is performed in response to a synchronization signal SYNC from the controller 101. Then, at times t60 to t69, sampling driving SD to read an image signal is performed. After that, the above-described read operation RO (see FIG. 4) is performed.

FIG. 6B is an enlarged view of the timing chart of the reset driving RD. In the reset driving RD, a reset operation of resetting the photodiode PD and an operation of holding a voltage corresponding to kTC noise in the clamp capacitor $C_{CL}$ are performed in response to the synchronization signal SYNC. First, at time t51, the enable signal EN is set to H level to turn on the transistors M3 and M6. Accordingly, the transistors M4 and M7 are set in a state to perform the source follower operation.

At time t52, the signal PRES is set to H level to turn on the transistor M2. The photodiode PD is thus connected to a reference voltage VRES and reset, and the voltage of the capacitor $C_{FD}$ is also reset. In addition, a voltage corresponding to the gate voltage of the transistor M4 at the time of reset is applied to one terminal n1 (the terminal on the side of the transistor M4) of the clamp capacitor $C_{CL}$.

At time t53, the signal PCL is set to H level to turn on the transistor M5. The clamp voltage VCL is thus applied to the terminal n2 (the terminal on the side of the transistor M7) of the clamp capacitor $C_{CL}$.

At time t54, the signal PRES is set to L level to turn off the transistor M2. The terminal n1 of the clamp capacitor $C_{CL}$ is thus set to the voltage corresponding to the gate voltage of the transistor M4 at the time of reset.

At time t55, the signal PCL is set to L level to turn off the transistor M5. Accordingly, charges (charges based on the potential difference between the reference voltage VRES and the clamp voltage VCL) corresponding to the potential difference between the terminals n1 and n2 are held by the clamp capacitor $C_{CL}$, and the kTC noise caused by the heat of the photodiode PD or the like is clamped.

At time t56, the enable signal EN is set to L level to turn off the transistors M3 and M6. Accordingly, the transistors M4 and M7 are set in an inoperative state. After that, the above-described exposure permission signal is set to H level.

The series of operations of the reset driving RD ends in this way. That is, in the reset driving RD, the photodiode PD is reset, and the clamp capacitor $C_{CL}$ is also reset. The reset clamp capacitor $C_{CL}$ holds a voltage corresponding to kTC noise. After that, radiation irradiation is performed, and charges corresponding to the radiation irradiation amount are generated in the photodiode PD. Note that the reset driving RD is performed at once for all sensors to prevent a shift of the control timing. Hence, the continuity of data is maintained between the sensor chips and between the sensors.

FIG. 6C is an enlarged view of the timing chart of the sampling driving SD. In the sampling driving SD, an operation of sampling and holding a signal level corresponding to the amount of charges generated in the photodiode PD in the capacitor CS as the S signal is performed. Additionally, in the sampling driving SD, an operation of sampling and holding a noise level corresponding to fitted pattern noise caused by the structure of the sensor s or the manufacturing variation of elements in the capacitor CN as the N signal is performed.

At time t60, the enable signal EN is set to H level to turn on the transistors M3 and M6. The transistors M4 and M7 are set in a state to perform the source follower operation. The gate voltage of the transistor M4 changes depending on the amount of charges generated and accumulated in the photodiode PD. A voltage corresponding to the changed gate voltage is input to the terminal n1 of the clamp capacitor $C_{CL}$, and the potential of the terminal n1 changes. Along with the change in the potential of the terminal n1, the potential of the terminal n2 of the clamp capacitor $C_{CL}$ changes.

At time t61, the signal TS is set to H level to turn on the transistor M8. The capacitor CS is thus charged with a voltage corresponding to the potential of the terminal n2 (the above-described changed potential of the terminal n2).

At time t62, the signal TS is set to L level to turn off the transistor M8. The voltage is thus fixed in the capacitor CS (sampling of the S signal). Additionally, at time t62, the exposure permission signal is set to L level. Note that the period of times t54 to t62 corresponds to the charge accumulation time of the photodiode PD. In this period, not only the charges in the amount corresponding to the radiation irradiation amount but also charges derived from a dark current or the like in an amount corresponding to the period are accumulated in the photodiode PD.

At time t63, the signal PCL is set to H level to turn on the transistor M5. The clamp voltage VCL is thus applied to the terminal n2 (the terminal on the side of the transistor M7) of the clamp capacitor $C_{CL}$.

At time t64, the signal PRES is set to H level to turn on the transistor M2. The voltage of the FD capacitor $C_{FD}$ is reset to the reference voltage VRES, and the voltage of the terminal n1 is also reset. After that, at time t65, the signal PRES is set to L level to turn off the transistor M2. The terminal n1 of the clamp capacitor $C_{CL}$ is thus set to the voltage corresponding to the gate voltage of the transistor M4 at the time of reset.

At time t66, a signal TN is set to H level to turn on the transistor M11. The capacitor CN is thus charged with a voltage corresponding to the potential (the above-described supplied voltage VCL) of the terminal n2. After that, at time t67, the signal TN is set to L level to turn off the transistor M11. The voltage is thus fixed in the capacitor CN (sampling of the N signal).

Finally, at time t68, the signal PCL is set to L level to turn off the transistor M5. At time t69, the enable signal EN is set to L level to turn off the transistors M3 and M6 (the transistors M4 and M7 are set in an inoperative state).

In summary, in the sampling driving SD, sampling of the S signal is performed from time t61 to t62, and reset of the photodiode PD and sampling of the N signal are performed from time t63 to t68.

The series of operations of the sampling driving SD ends in this way. That is, in the sampling driving SD, a signal level corresponding to the amount of charges generated in the photodiode PD is sampled and held in the capacitor CS as the S signal, and a noise level corresponding to fitted pattern noise is sampled and held in the capacitor CN as the N signal. Note that the sampling driving SD can be performed at once for all sensors, like the above-described reset driving RD.

After that, the S signal and the N signal are read by the read operation RO performed after the sampling driving SD, as described above. The difference between the signals is A/D-converted, and frame data is formed based on the group of the A/D-converted signals.

Referring back to FIG. 6A, in the reset driving RD and the sampling driving SD, the power consumption increases from PW1 to PW2, as will be described later in detail. The power consumption can be calculated based on the amount of a current flowing from the power supply voltage to the ground voltage. The power consumption increases from PW1 to PW2 mainly because the enable signal EN is set to H level to set the transistors M4 and M7 in the source follower operation state.

Figure 7:
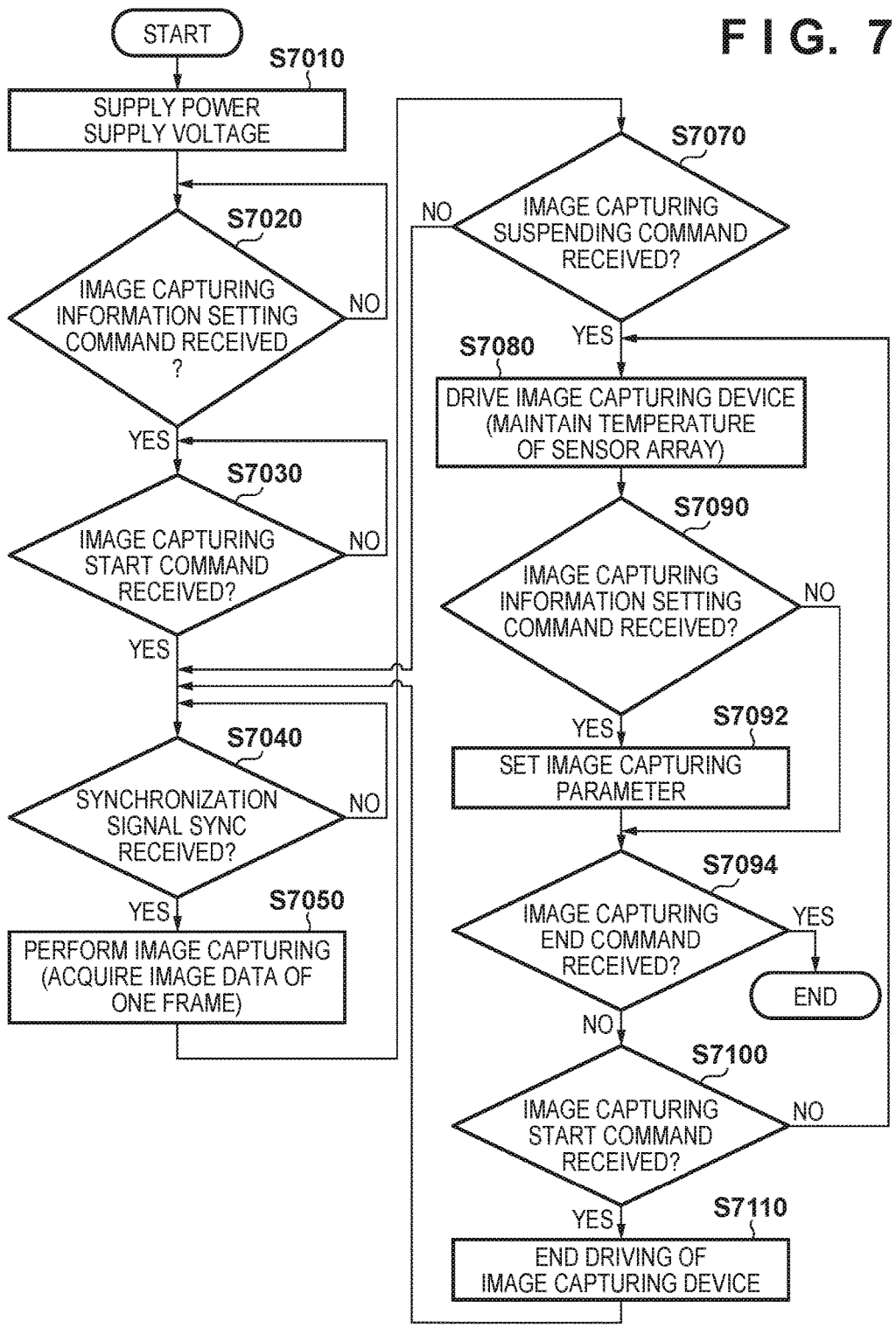
FIG. 7 is a flowchart for explaining an example of a method of controlling the radiation imaging apparatus.

FIG. 7 shows the control method (flowchart) of the apparatus IA. Note that control according to the flowchart is substantially executed by the image capturing controller 109 upon receiving the above-described instruction by a control signal or control command from the controller 101. However, the control may partially be executed by the controller 101.

In step S7010 (to be simply referred to as S7010 hereinafter, and ditto for other steps), the power supply voltage is supplied to the apparatus IA. Until the supplied power supply voltage stabilizes (substantially becomes constant), the apparatus IA is maintained in a standby state. A sensor signal can include a noise component derived from heat. To prevent a signal value from changing due to a temperature variation of the sensor s, the temperature of the sensor array 105 preferably stabilizes in S7010.

In S7020, it is determined whether a command (image capturing information setting command) to set image capturing information input by the user is received. This command is input via the control interface 110. If the command is received, parameters and the like according to the image capturing information are set in a register (not shown) in the image capturing controller 109, and the process advances to S7030. Otherwise, the standby state is maintained until the command is received. The frame rate of radiographic imaging (in this example, movie capturing or continuous capturing) to be described later is decided based on the parameters and the like set in S7020.

In S7030, it is determined whether a command (image capturing start command) to start radiographic imaging is received. This command is input via the control interface 110. If the command is received, the process advances to S7040. Otherwise, the standby state is maintained until the command is received.

In S7040, it is determined whether the synchronization signal SYNC is received. If the synchronization signal SYNC is received, the process advances to S7050. Otherwise, the standby state is maintained until the synchronization signal SYNC is received.

In S7050, one radiographic imaging is performed in response to the reception of the synchronization signal SYNC, and frame data (image data of one frame) is acquired. That is, as described with reference to FIGS. 6A to 6C, after the reset driving RD, the exposure permission signal changes to active level (radiation irradiation is performed for a predetermined period), the sampling driving SD is performed, and then, the read operation RO is performed as described with reference to FIG. 4.

By the series of operations in S7040 and S7050, one frame data is obtained. The series of operations can be expressed as an image acquisition operation. Movie capturing or continuous capturing is implemented by repeating the series of operations and acquiring a plurality of frame data. The series of operations is repeated at the frame rate set in S7020. That is, the synchronization signal SYNC is supplied at a period corresponding to the frame rate set in S7020.

In S7070, it is determined whether a command (image capturing suspending command) to suspend radiographic imaging is received. This command is input to pause movie capturing or suspend continuous capturing to, for example, observe details of the morbid portion of the subject. If the command is received, the process advances to S7080. Otherwise, the process returns to S7040 (that is, radiographic imaging is continued). Note that if the command is received, image capturing is suspended, and radiographic imaging is not performed. Hence, the periodical supply of the synchronization signal SYNC is also suspended.

In S7080, the image capturing device 100 is driven, thereby suppressing lowering of the temperature of the sensor array 105. More specifically, during a suspension of radiographic imaging, the image capturing device 100 is driven to prevent power consumption in the image capturing device 100 (in particular, the sensor array 105) from lowering, thereby maintaining the temperature of the sensor array 105. In S7080, the reset driving RD, the sampling driving SD, and the read operation RO are performed as in S7050, as will be described later in detail. In S7080, however, since image capturing is suspended, and radiographic imaging is not performed, the exposure permission signal does not change to active level (that is, radiation irradiation is not performed).

To suppress lowering of the temperature of the sensor array 105 (or to maintain the temperature), the image capturing device 100 is periodically driven. In this example, the period of driving is a period corresponding to the frame rate set in S7020. The method of deciding the period of driving of the image capturing device 100 is not limited to this example. In another example, the image capturing device 100 may is driven at a fixed period or may be driven based on the temperature of the sensor array 105 (for example, a measurement result obtained by a temperature sensor).

In S7090, it is determined whether an image capturing information setting command is received, as in S7020. This command is input as new image capturing information before resumption of radiographic imaging. The new image capturing information may be the same as the image capturing information set in S7020. If the command is received, the process advances to S7092. Otherwise, the process advances to S7094.

In S7092, parameters and the like according to the new image capturing information are set in the register (not shown) in the image capturing controller 109 based on the image capturing information setting command received in S7090.

In S7094, it is determined whether a command (image capturing end command) to end radiographic imaging is received. If the command is received, control of the apparatus IA according to the flowchart ends. Otherwise, the process advances to S7100.

In S7100, it is determined whether a command (image capturing start command) to resume radiographic imaging is received. This command is the same command as the image capturing start command in S7030, but may be a different command (for example, image capturing resuming command). If the command is received, the process advances to S7110. Otherwise, the process returns to S7080.

In S7110, driving of the image capturing device 100 in S7080 ends, and the process returns to S7040 (that is, radiographic imaging is resumed).

Note that if the image capturing information newly set in S7092 is different from the image capturing information set in S7020, and the process returns from S7100 to S7080, the period of driving of the image capturing device 100 to maintain the temperature of the sensor array 105 can be changed. More specifically, the period of driving of the image capturing device 100 can be changed to a period corresponding to a new frame rate based on the newly set image capturing information. This can suppress the temperature variation of the sensor array 105 when resuming radiographic imaging at the new frame rate.

FIG. 8A is a flowchart for explaining control by the image capturing controller 109 in a capturing mode. FIG. 8B is a flowchart for explaining control in a non-capturing mode. The capturing mode (first mode) is an operation mode to execute control corresponding to S7040 and S7050. This is the operation mode to repetitively execute the image acquisition operation. The non-capturing mode (second mode) is an operation mode to execute control corresponding to S7080. This is the operation mode not to execute the image acquisition operation.

Referring to the flowchart of the capturing mode shown in FIG. 8A, in S8010, it is determined whether the synchronization signal SYNC is received. If the synchronization signal SYNC is received, the process advances to S8020. Otherwise, the standby state is maintained until the synchronization signal SYNC is received. In S8020, the reset driving RD is executed (see FIGS. 6A to 6C). In S8030, the exposure permission signal changes to active level (the start of radiation irradiation is requested, and radiation irradiation is performed for a predetermined period). In S8040, the sampling driving SD is executed. In S8050, the read operation RO is executed (see FIG. 4). In S8060, it is determined whether to end the capturing mode. To end the capturing mode, control according to the flowchart ends. Otherwise, the process returns to S8010 (that is, S8020 to S8050 are executed every time the synchronization signal SYNC is received).

The non-capturing mode will be described next. As described with reference to FIG. 7 (S7070), if the image capturing suspending command is received, that is, in the non-capturing mode, the synchronization signal SYNC is not supplied. The image capturing controller 109 periodically generates an internal synchronization signal (to be referred to as an internal synchronization signal SYNCX hereinafter) as a signal that replaces the synchronization signal SYNC, as will be described later in detail.

Referring to the flowchart of the non-capturing mode shown in FIG. 8B, in S8110, it is determined whether the internal synchronization signal SYNCX is received. If the internal synchronization signal SYNCX is received, the process advances to S8120. Otherwise, the standby state is maintained until the internal synchronization signal SYNCX is received. S8120 to S8150 are the same as S8020 and S8040 to S8060 in the capturing mode. That is, in the non-capturing mode, the same driving control as in the capturing mode is performed in steps after reception of the internal synchronization signal SYNCX, except that S8030 (the step of changing the exposure permission signal to active level) is not executed.

Figure 9:
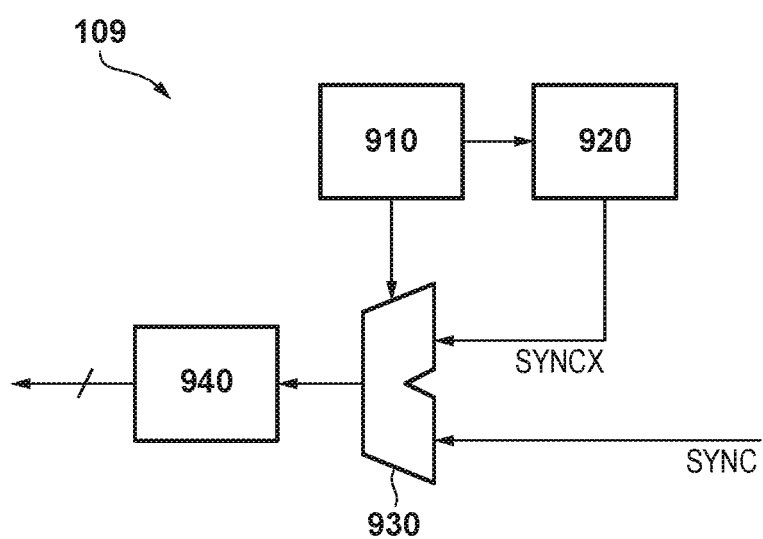
FIG. 9 is a view for explaining an example of the arrangement of the image capturing controller.

FIG. 9 shows a part of the arrangement of the image capturing controller 109. The image capturing controller 109 includes a setting unit 910, a synchronization signal generator 920, a selector 930, and a control signal generator 940. A parameter according to the operation mode is set in the setting unit 910. The synchronization signal generator 920 periodically generates the internal synchronization signal SYNCX based on the parameter. The period of generation of the internal synchronization signal SYNCX by the synchronization signal generator 920 is the period corresponding to the frame rate of radiographic imaging, as described above. Note that information representing the frame rate is set in the setting unit 910 together with the parameter.

The selector 930 is controlled based on the parameter. That is, according to the operation mode, the selector 930 outputs one of the synchronization signal SYNC from the controller 101 and the internal synchronization signal SYNCX from the synchronization signal generator 920 to the control signal generator 940.

Using the signal from the selector 930 as a trigger, the control signal generator 940 generates various kinds of control signals (see FIGS. 4 and 6A to 6C) to drive the sensor unit 10 and the reader 20. The control signal generator 940 is formed using, for example, a shift register. The control signal generator 940 receives the signal from the selector 930 as a start pulse signal, and in response to this, generates the various kinds of control signals in a predetermined order. More specifically, the control signal generator 940 generates the various kinds of control signals using the synchronization signal SYNC as a trigger in the capturing mode and using the internal synchronization signal SYNCX as a trigger in the non-capturing mode. Hence, as described above, the same driving control is performed in the image capturing device 100 in both the capturing mode and the non-capturing mode.

With this arrangement, during the non-capturing mode, the image capturing device 100 can be driven to prevent power consumption in the image capturing device 100 (in particular, the sensor array 105) from lowering, thereby maintaining the temperature of the sensor array 105. Hence, according to this arrangement, it is possible to suppress the variation in the noise component of the sensor signal caused by the variation in the temperature and prevent image quality from changing when the mode shifts to the capturing mode to resume radiographic imaging.

Even in the non-capturing mode, frame data is obtained from the sensor array 105 because the same driving control as in the capturing mode is performed in the image capturing device 100. However, in the non-capturing mode, radiation irradiation is not performed. For this reason, the frame data obtained in the non-capturing mode includes no signal component. Frame data obtained in the non-capturing mode will be expressed here as "dummy data" for the sake of discrimination from frame data obtained in the capturing mode. The dummy data is secondary data obtained by the driving to maintain the temperature of the sensor array 105. Hence, the dummy data is discarded in the image capturing controller 109 (or the controller 101). Note that since the dummy data is dark image data acquired without radiation irradiation, in another example, the dummy data may be, for example, held in a memory and used as data for offset correction (the dummy data need not always be discarded).

In this example, the change of the operation mode (capturing mode/non-capturing mode) is implemented in response to reception of an operation mode change instruction (command or signal) such as the image capturing suspending command or image capturing start command described with reference to FIG. 7, but may be implemented by another method. For example, in the capturing mode, if the synchronization signal SYNC is not input for a predetermined period, the operation mode may forcibly be changed to the non-capturing mode. Additionally, for example, in the non-capturing mode, if supply of the synchronization signal SYNC starts, the operation mode may forcibly be changed to the capturing mode. In both operation modes, since the control signal generator 940 generates the control signals in a predetermined order, and the same driving control is performed in the image capturing device 100, the shift of the operation mode can be implemented in a relatively short time. Additionally, driving control of the image capturing device 100 according to the non-capturing mode may be executed before the start of the first radiographic imaging (for example, in a step between S7020 and S7030 in FIG. 7). In this example, the change of the operation mode is implemented in response to reception of the image capturing suspending command and the image capturing start command. However, the present invention is not limited to this, and the change of the operation mode may be implemented in response to reception of the image capturing resuming command and the image capturing end command.

FIGS. 10A and 10B show the driving method (timing charts) of the sensor s when changing the operation mode (capturing mode/non-capturing mode). FIG. 10A shows a comparative example, and FIG. 10B shows an example (to be referred to as this example hereinafter) of the driving method according to the control shown in FIG. 7. The abscissa in FIGS. 10A and 10B represents the time axis. FIGS. 10A and 10B show that the apparatus operates in the capturing mode during a period T101, operates in the non-capturing mode during a period T102, and operates in the capturing mode again during a subsequent period T103.

Average power consumption and apparatus temperature (in particular, the temperature of the sensor array 105) in each operation mode are plotted along the ordinate as well as the various kinds of signals SYNC and the like and power consumption described with reference to FIGS. 6A to 6C. The average power consumption may be referred to as effective power consumption and can be calculated by dividing the integrated value of power consumption in the period of a certain operation mode by the period. In general, the apparatus temperature depends on the average power consumption. For example, if the average power consumption increases, the apparatus temperature then rises accordingly. If the average power consumption decreases, the apparatus temperature then lowers accordingly.

Let PW_AVE1 be the average power consumption in the capturing mode during the period T101, PW_AVE2 be the average power consumption in the non-capturing mode during the period T102, and PW_AVE3 be the average power consumption in the capturing mode during the period T103. Also, let TEMP_AVE1 be the apparatus temperature in the capturing mode during the period T101, TEMP_AVE2 be the apparatus temperature in the non-capturing mode during the period T102, and TEMP_AVE3 be the apparatus temperature in the capturing mode during the period T103.

Referring to FIG. 10A, in the non-capturing mode of the comparative example, the signal levels of the various signals do not substantially change, that is, the image capturing device 100 is maintained at rest. For this reason, the average power consumption PW_AVE2 in the period T102 (non-capturing mode) is smaller than the average power consumption PW_AVE1 in the period T101 (capturing mode). If the mode shifts to the capturing mode again in the period T103 after that, the average power consumption PW_AVE3 (=PW_AVE1) is larger than PW_AVE2. Hence, according to the comparative example, immediately after the mode shifts to the non-capturing mode in the period T102, the apparatus temperature TEMP_AVE2 lowers from TEMP_AVE1. Immediately after the mode shifts to the capturing mode again in the period T103, the apparatus temperature TEMP_AVE3 rises from TEMP_AVE2. For this reason, according to the comparative example, immediately after the mode shifts to the capturing mode in the period T103, the noise component of the sensor signal varies due to the temperature variation, and the image quality changes.

On the other hand, referring to FIG. 10B, in this example, the same driving control is done in the image capturing device 100 in both the capturing mode and the non-capturing mode. For this reason, the average power consumption PW_AVE2 in the period T102 (non-capturing mode) remains substantially equal to the average power consumption PW_AVE1 in the period T101 (capturing mode). If the mode shifts to the capturing mode again in the period T103, the average power consumption PW_AVE3 substantially equals PW_AVE2. Hence, according to this example, the apparatus temperature does not substantially change throughout the periods T101 to T103 (TEMP_AVE1≈TEMP_AVE2≈TEMP_AVE3). Hence, according to this example, the temperature variation immediately after the mode shifts to the capturing mode in the period T103 is suppressed. It is therefore possible to suppress the variation in the noise component of the sensor signal caused by the temperature variation and suppress the change in the image quality when resuming radiographic imaging.

Note that as another example, a method of controlling the apparatus temperature using a heater and a fan can also be considered. According to this example, in the non-capturing mode, driving control of the image capturing device 100 is performed as in the capturing mode. Hence, the apparatus temperature in the non-capturing mode can be made close to the target value relatively easily. However, it is not necessary to perform completely the same driving control in the capturing mode and the non-capturing mode. Driving for a portion that does not substantially has the influence on the variation in the above-described power consumption or the apparatus temperature may be suppressed.

The average power consumption PW_AVE2 is set to suppress the change in the image quality, that is, to make the apparatus temperature TEMP_AVE2 close to TEMP_AVE1. Hence, the average power consumption PW_AVE2 preferably substantially equals PW_AVE1 (=PW_AVE3). However, for example, if the average power consumption PW_AVE2 falls within the range of ±20% of PW_AVE1, the change in the image quality can sufficiently be changed. More preferably, the average power consumption PW_AVE2 falls within the range of ±10% of the power consumption PW_AVE1.

Several preferred embodiments and modifications have been described above. These embodiments and modifications have been shown only for the purpose of explaining the present invention, and the present invention may be modified without departing from the scope of the invention. Individual terms described in this specification are merely used for the purpose of explaining the present invention, and the present invention is not limited to the strict meanings of the terms and can also incorporate their equivalents.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-105444, filed on May 26, 2016, which is hereby incorporated by reference herein in its entirety.

What is claimed is:

1. A radiation imaging apparatus comprising:
an image capturing device comprising a sensor array having a plurality of sensors arranged in an array; and
a controller comprising a signal generator and being configured to perform a control so as to drive the image capturing device in response to a trigger, wherein
the controller is configured to perform radiographic imaging by executing repetitively an operation for obtaining image data of one frame from the sensor array at a period corresponding to a predetermined frame rate, the operation being performed by driving the image capturing device so as to be synchronized with one radiation irradiation for the sensor array,
the controller is configured to shift to a non-capturing mode upon receiving an instruction representing a suspension of the radiographic imaging,
the controller is configured to shift to a capturing mode upon receiving an instruction representing a start of the radiographic imaging,
the controller is configured to drive the image capturing device using a synchronization signal as the trigger in the capturing mode, the synchronization signal being for a synchronous controlling between the operation and the radiation irradiation repeated at the period,
the signal generator is configured to generate another signal differing from the synchronization signal when the controller is in the non-capturing mode, and
the controller drives the image capturing device using the other signal as the trigger instead of using the synchronization signal in the non-capturing mode, thereby suppressing lowering of a temperature of the sensor array in the non-capturing mode from the temperature of the sensor array in the capturing mode.

2. The apparatus according to claim 1, wherein the controller is configured to shift from the capturing mode to the non-capturing mode when suspending the radiographic imaging, and is configured to shift from the non-capturing mode to the capturing mode when starting the suspended radiographic imaging.

3. The apparatus according to claim 1, wherein the controller is configured to periodically drive the sensor array in the non-capturing mode.

4. The apparatus according to claim 1, wherein the signal generator is configured to generate the other signal, based on one of:
(i) a period at which the controller receives the synchronization signals;
(ii) a fixed period; or
(iii) a period based on a temperature of the sensor array.

5. The apparatus according to claim 4, wherein the signal generator is configured to periodically generate the other signal when the controller receives one of a signal and a command as the instruction representing the suspension of the radiographic imaging.

6. The apparatus according to claim 1, wherein the controller is configured to drive the image capturing device based on a temperature of the sensor array in the non-capturing mode.

7. The apparatus according to claim 1, wherein the controller is configured to hold a signal obtained by driving the image capturing device in a memory as a signal for offset correction in the non-capturing mode.

8. The apparatus according to claim 1, wherein the image capturing device further comprises a first circuit unit configured to drive the plurality of sensors and a second circuit configured to read out signals from the plurality of sensors,
- each of the plurality of sensors including a detection element configured to detect a radiation, and a plurality of elements configured to output a signal of the detection element, and
- the plurality of elements are adapted to be driven in the same order in the capturing mode and the non-capturing mode by the first circuit unit, while a voltage is applied to the detection element of each of the plurality of sensors.

9. The apparatus according to claim 1, wherein average power consumption of the sensor array in the non-capturing mode falls within a range of ±20% of average power consumption of the sensor array in the capturing mode.

10. The apparatus according to claim 1, wherein the sensor array is formed by a CMOS image sensor chip.

* * * * *